United States Patent
Eck et al.

(10) Patent No.: US 7,454,043 B2
(45) Date of Patent: Nov. 18, 2008

(54) IMAGE PROCESSING UNIT AND METHOD OF ASSOCIATING STORED IMAGES WITH CURRENT IMAGES

(75) Inventors: Kai Eck, Aachen (DE); Geert Gijsbers, Best (NL); Sabine Mollus, Aachen (DE)

(73) Assignee: Koninklijke Philips Electronics N.V., Eindhoven (NL)

(*) Notice: Subject to any disclaimer, the term of this patent is extended or adjusted under 35 U.S.C. 154(b) by 254 days.

(21) Appl. No.: 10/530,816

(22) PCT Filed: Oct. 2, 2003

(86) PCT No.: PCT/IB03/04339

§ 371 (c)(1), (2), (4) Date: Feb. 28, 2006

(87) PCT Pub. No.: WO2004/034329

PCT Pub. Date: Apr. 22, 2004

(65) Prior Publication Data
US 2006/0120581 A1    Jun. 8, 2006

(30) Foreign Application Priority Data
Oct. 10, 2002    (DE)    ................. 102 47 299

(51) Int. Cl.
*G06K 9/00*    (2006.01)
(52) U.S. Cl. ............... 382/128; 382/131; 382/132; 382/232; 378/99; 378/95; 378/98; 378/114; 600/413
(58) Field of Classification Search ............... 600/413; 382/128, 131, 132, 232; 604/407; 378/99, 378/95, 98, 114, 54, 6
See application file for complete search history.

(56) References Cited

U.S. PATENT DOCUMENTS

| | | | | |
|---|---|---|---|---|
| 4,204,225 | A * | 5/1980 | Mistretta | 378/98.12 |
| 4,709,385 | A * | 11/1987 | Pfeiler et al. | 378/98.12 |
| 5,274,551 | A | 12/1993 | Corby, Jr. | |
| 5,694,316 | A * | 12/1997 | Azancot | 382/232 |
| 6,332,014 | B1 * | 12/2001 | Boutenko et al. | 378/95 |
| 6,370,417 | B1 * | 4/2002 | Horbaschek et al. | 600/424 |
| 6,473,635 | B1 | 10/2002 | Rasche | |
| 6,798,199 | B2 * | 9/2004 | Larson et al. | 324/309 |
| 2002/0137014 | A1 * | 9/2002 | Anderson et al. | 434/262 |
| 2006/0171575 | A1 * | 8/2006 | Eckert et al. | 382/128 |

FOREIGN PATENT DOCUMENTS
DE    19946948    4/2001

(Continued)

OTHER PUBLICATIONS
Beier et al Advanced Subtraction Angiography, Mask selection and image registration), IEEE 1994.*

(Continued)

*Primary Examiner*—Andrew W. Johns
*Assistant Examiner*—Nancy Bitar

(57) ABSTRACT

The invention relates to the association of a current (X-ray image) image of a body volume with one of several stored previous images, the ECG and the respiratory cycle being determined each time together with the images. Using this data, that one of the previous images is chosen which is closest to the current image in respect of cardiac rhythm and respiratory cycle. The resultant association yields a very high accuracy enabling superposed reproduction of the current image and the associated previous image.

20 Claims, 2 Drawing Sheets

FOREIGN PATENT DOCUMENTS

Figure 1:
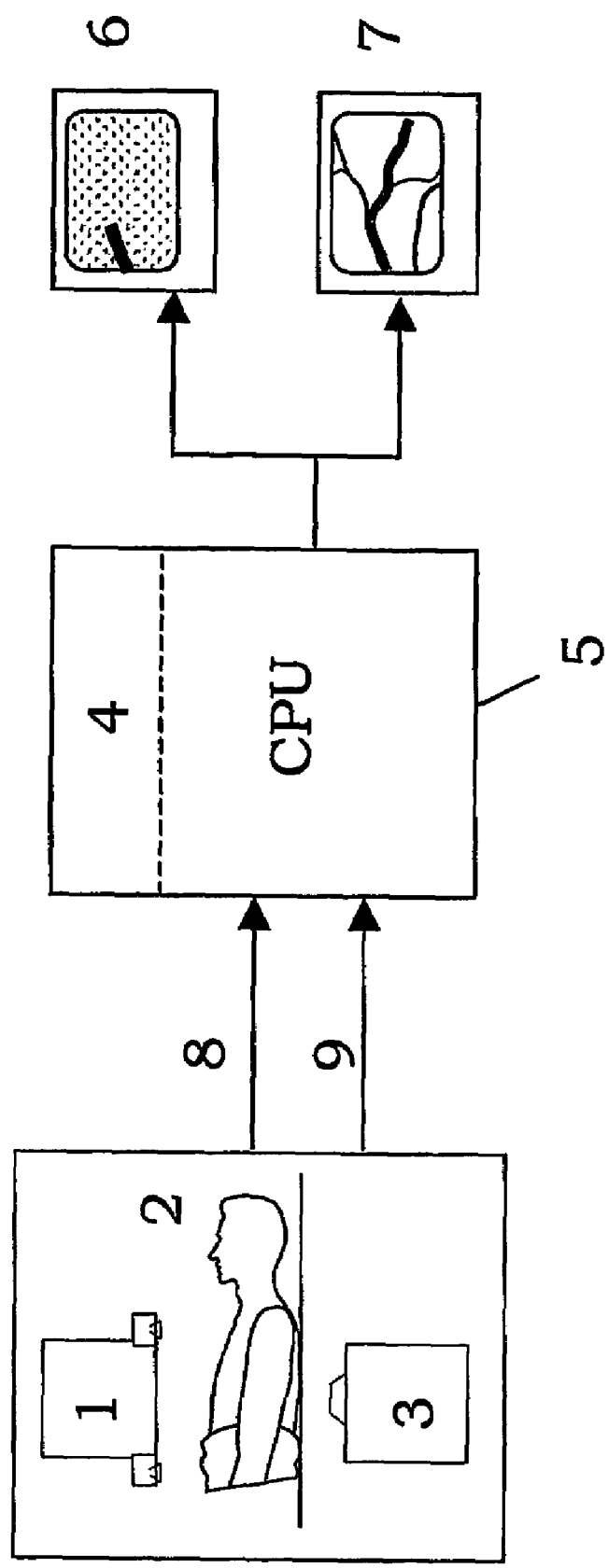

DE    19946948 A1    4/2001
FR    2562743 A1    10/1985

OTHER PUBLICATIONS

J. Beier, et al: Advanced Subtraction Angiography: Mask Selection and Image Registration, IEEE Sep. 1994, pp. 105-108, XP010147930.

Nadkarni S. K. et al: Image-Based Retrospective Cardiac Gating for Three-Dimensional Intravascular Ultrasound Imaging, SPIE vol. 4687, Feb. 2002, pp. 276-284, XP002272220.

Beier, J., et al.; Advanced Subtraction Angiography: Computers in Cardiology;1994; pp. 105-108.

Nadkarni, S.K., et al.; Image-based Retrospective Cardiac Gating for Three-Dimensional; Medical Imaging; 2002; pp. 276-284.

* cited by examiner

IMAGE PROCESSING UNIT AND METHOD OF ASSOCIATING STORED IMAGES WITH CURRENT IMAGES

The invention relates to an image processing unit which comprises an input for the signal of a current image of a body volume, the body volume being subject to a motion comprising several phases of motion, an input for a signal which represents the phase of motion of the current image, and a memory in which previous images of the body volume are stored together with the associated phases of motion. The invention also relates to a method of associating a current image of a body volume, being subject to a motion comprising different phases of motion, with a previous image of the body volume.

The imaging of body volumes is practiced notably in the field of medical diagnostics and therapy, that is, in the context of X-ray fluoroscopy. Therefore, the X-ray projection of a biological body volume will be considered hereinafter by way of example, be it that the present invention is by no means restricted thereto and can be used in all fields of application with similar secondary conditions.

A special medical application is formed by the X-ray fluoroscopic observation of the propagation of a catheter in the vascular system of a patient. The tip of the catheter should then be advanced as accurately as possible into a region of interest to be treated or examined, for example, a stenosis, or a guide wire should be positioned behind said region of interest in such a manner that the tip of the catheter is correctly positioned. In this respect it is known to display angiographic images of the body volume on a second monitor adjacent the current image of the body volume. The angiographic images reproduce the vessels in a highlighted fashion and can be acquired, for example, by utilizing a contrast agent. The still angiographic image supports the orientation for the attendant physician as a "vascular map" or "road map" of the vascular system. However, the known methods are not suitable to achieve a desirable exact association of corresponding locations in the angiographic image and the current image, that is, with an accuracy in the millimeter or sub-millimeter range, because the body volume of a patient being observed usually is subject to a more or less strong (natural) motion which is caused notably by heartbeat and respiration.

In this respect it is known from DE 199 46 948 A1 to acquire in advance three-dimensional images of the body organ in different phases of its motion in order to determine the position of an instrument, for example, a catheter, relative to a moving body organ, for example, the heart, the phase of motion being determined and described by way of an electrocardiogram (ECG) which is recorded in parallel. During the current medical intervention the position of the catheter is then measured together with the associated phase of the electrocardiogram and the catheter is reproduced in that three-dimensional image which is associated with the same phase of the electrocardiogram of the body organ. However, this method necessitates on the one hand three-dimensional images of the body volume and on the other hand does not involve the continuous fluoroscopic monitoring of the medical intervention.

Considering the foregoing it is an object of the present invention to provide a method and a device which enable stored images of a body volume to be associated with a current image with a high precision which is preferably in the millimeter or sub-millimeter range.

This object is achieved by means of an image processing unit which is characterized as disclosed in claim 1 as well as by means of a method which is characterized as disclosed in claim 9. Advantageous embodiments are disclosed in the dependent claims.

The image processing unit in accordance with the invention comprises:

an input for the signal of a "current image" of a body volume, which body volume is subject to a motion involving different phases of motion. The image may have been formed in particular by means of an X-ray apparatus with an X-ray source and an X-ray detector. However, the image may also have been acquired by means of other methods, such as magnetic resonance, ultrasound, scintigraphy or the like. The term "current image" represents the normal situation in which this image is acquired and transferred on-line, that is in real time, be it that applications with "off-line" processing should not be excluded.

An input for a signal which represents the phase of motion of the body volume during said current image.

A memory in which "previous images" of the body volume are stored together with the respective associated phases of motion. The previous images may have been acquired by means of the same imaging device which also generates the current image of the body volume. However, it is also possible for the previous images to originate from other sources. In the context of a medical intervention of the kind set forth, the previous images may notably be angiographic images in which the vascular system in the relevant body volume is represented.

The image processing unit is arranged to associate with the current image that one of the previous images whose phase of motion is closest to the phase of motion of the current image.

The image processing unit in accordance with the invention enables very accurate association of a previously stored image of a body volume with a current image of the body volume, because the phases of motion of the associated images are as close as possible to one another, thus minimizing the motion-induced deviations between the images of the body volume.

In conformity with a further embodiment of the image processing unit it is arranged to determine the distance between the phases of motion of the current image and the associated previous image and to reproduce it for a user. Additionally, or alternatively, the image processing unit may also be arranged to determine the time elapsed since the last update of the association between current images and a previous image and to reproduce it for a user. The reproduction of the distance between the phases of motion and/or the time elapsed since the last association provides the user with information as to how up to date or exact the existing association still is. Therefore, on the basis of this representation the user can determine to what extent local correspondences of the images can still be trusted.

In the context of a special embodiment of the image processing unit, the body volume is a biological body volume such as, for example, the heart of a patient, and the motion of this body volume is caused by the heartbeat and/or the respiration. Heartbeat and respiration constitute two important causes of (natural) motions which have an effect throughout the body. The special image processing unit is characterized in that the phases of motion are described by an electrocardiogram (ECG) and/or the signal of a respiration sensor.

In conformity with a preferred embodiment of the invention, the image processing unit is arranged to carry out the following steps of the method:

calculation of a similarity measure between the current image and a predetermined representative image, calculation of the corresponding similarity measures between the representative image and the previous images or a sub-quantity of the previous images, selection of a sub-quantity which contains exactly those previous images whose similarity measure relative to the representative image is in a predetermined range around the similarity measure of the current image relative to the representative image.

According to this approach, therefore, all previous images are determined which are "just as similar or dissimilar" relative to the representative image as the current image, that is, all previous images which have the same similarity gap relative to the representative image as the current image. Therefore, the sub-quantity which will notably include also the images which are very similar to the current image. The method has the advantage that, after a representative image has been defined, all similarity measures between this representative image and the previous images have to be calculated only once after which they can be stored. The similarity measure has to be calculated anew again only for the current image. The sub-quantity, therefore, can be defined with little effort during operation.

For the above embodiment of the invention it is necessary to perform a suitable definition of the similarity of images or the similarity measure. A preferred similarity measure consists in the calculation of the histogram energy of the difference image between the two images. In this case a small value of the similarity measure stands for a high degree of similarity and vice versa.

A further embodiment of the image processing unit is arranged to carry out the following steps of the method:

calculation of the similarity measures between the current image and the previous images or a sub-quantity thereof;

selection of those previous images whose similarity to the current image exceeds a predetermined threshold value.

Thus, via a direct individual comparison it is determined which of the previous images are particularly similar to the current image. This approach is advantageously combined with the previously described determination of a sub-quantity (by similarity comparison with a representative image) in that the individual comparison is carried out only with the elements of the sub-quantity. The calculation-intensive determination of similarity measures can thus be minimized.

In the context of a preferred embodiment of the invention, the complete electrocardiogram over the duration of at least one heartbeat as well as the instant of acquisition of the previous image in relation to this ECG are stored together with each previous image. Furthermore, the image processing unit is arranged to determine a transformation which maps (transforms) the electrocardiogram recorded parallel to the current image on the electrocardiogram of a previous image. Using this transformation, the relative position of the phase of motion of the current image is determined in relation to the phase of motion of the previous image. The transformation used should point-wise associate two different electrocardiograms with one another in an optimum fashion while equalizing insignificant variations in time of the physiological potentials. After determination of such an optimum transformation, a given point in an electrocardiogram can be associated as well as possible with the corresponding point the other electrocardiogram. For this association it is important that the transformation takes into account the entire electrocardiogram over a period (heartbeat).

A further embodiment of the image processing unit is arranged to carry out a motion correction between the associated images (current image and a previous image), which correction takes into account a motion of the entire body volume. In the context of medical applications, such overall motions may arise notably due to a change of position of the patient. Such overall motions are generally incidental and, therefore, do not contain regularities that can be detected during the correction of (natural) motions of the body volume.

The image processing unit may be coupled in particular to a reproduction unit such as, for example, a monitor or a printer, and be arranged to reproduce the current image of the body volume and the associated previous image in superposed form on the reproduction unit. Because of the described construction of the image processing unit, a high degree of precision is achieved for the correspondence between the current image and the associated previous image, so that they can be very accurately superposed. In the context of a medical application, for example, a physician can then derive from a previous angiographic image the vascular tree which is then added to the current image of the body volume which shows the instrument (catheter etc.). Because of the high degree of accuracy of the association, very exact positioning of the instrument can thus be performed. The previous image may especially also be an image from a preceding step of the same medical intervention, for example, the image of a stenosis before or during dilatation by means of a bulb catheter, or of the position of an already introduced first stent. The superposition of such a previous image enables the physician to find the previous position exactly, for example, so as to place a stent in the dilatated stenosis or in the vicinity of a first, already inserted stent.

The invention also relates to a device for generating and processing images of a body volume, which device includes a device for image acquisition, such as notably an X-ray apparatus as well as an image processing unit of the kind set forth. Furthermore, this device may also include sensors for the acquisition of a signal representing the phase of motion, notably an electrocardiograph and/or a respiration sensor (abdominal belt etc.).

The invention also relates to a method of associating a current image of a body volume, which is subject to motion comprising different phases of motion with one of several previous images of the body volume, in which method the phase of motion is determined together with the respective (previous and current) images, the current image is associated with that one of the previous images whose phase of motion is closest to the phase of motion of the current image.

As has already been described in conjunction with the image processing unit, the method offers the advantage that for the association of the current image with a previous image it takes into account the phases of motion of the body volume at which the images have been acquired. Changes of position as caused by the motion of the body are thus minimized.

The method can be extended by determining the distance between the phases of motion of the associated images and/or the time elapsed since the last update of the association between current image and a previous image, so as to reproduce this distance or time for the user. Reproduction is preferably performed by means of graphical visualization means such as a time bar, the fading of the previous image, or color encoding.

The invention can also be extended by way of the steps described in conjunction with the construction of the image processing unit.

Figure 2:
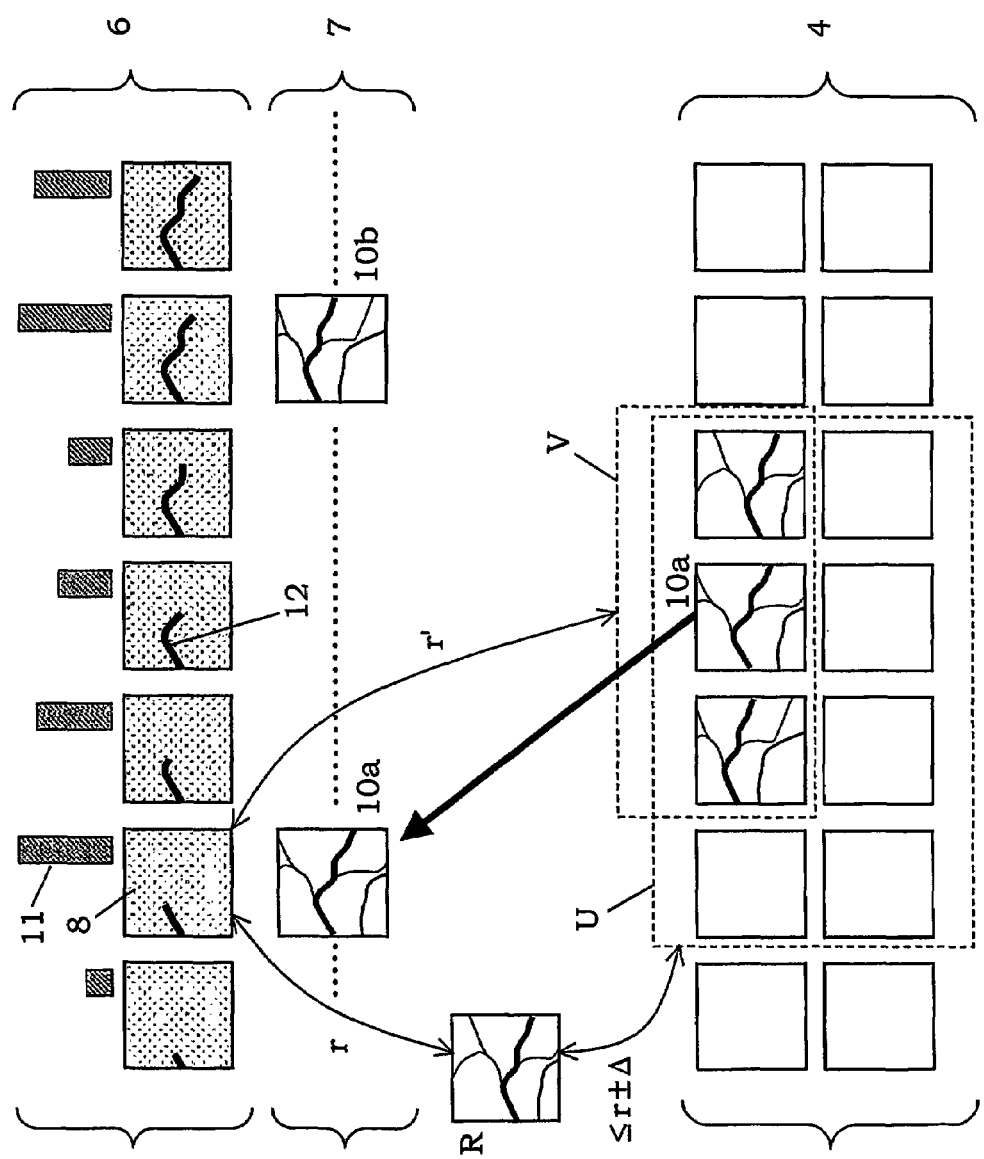

The invention will be described in detail hereinafter with reference to the Figures. Therein:

FIG. 1 shows an X-ray apparatus provided with an image processing unit in accordance with the invention, and FIG. 2 illustrates the principle of operation of the device in accordance with the invention on the basis of exemplary images.

The invention will be described in detail hereinafter on the basis of a medical application, however, without the invention being restricted in any way to this field. FIG. 1 is a diagrammatic representation of an X-ray apparatus with an X-ray source 3 and an X-ray detector 1 which are mounted at the ends of a C-arm (not shown) and form an X-ray image of the body volume of a patient 2 arranged therebetween. This image is applied as the current fluoroscopic image 8 to an image processing unit 5 (in real time).

At the same time the ECG of the patient 2 as well as a variable representing the respiratory cycle is acquired and presented to the image processing unit 5 in the form of signals 9.

The image processing unit 5 comprises a memory 4 in which previous images of the body volume of the patient 2 are stored. Such images may notably be angiographic images which have been acquired by means of the X-ray apparatus 1, 3 while utilizing a contrast medium and which represent the vascular tree in the body volume in highlighted form. The previous images may also have been acquired by means of other equipment (MR, ultrasound, scintigraphy or the like). Furthermore, the previous images may also be buffered images or image sequences concerning the current intervention which have been acquired by means of the X-ray apparatus 1, 3. Images of this kind can reproduce in particular the position of an instrument, such as that of a catheter which has been introduced into the vascular system of the patient and has a catheter tip, or of a guide wire.

The image processing unit 5 is also coupled to (at least) two monitors 6, 7 and is arranged to display the current image 8 "live" on both monitors 6, 7 and to display on the monitor, superposed thereon, one of the previous images derived from the memory 4. The parallel (superposed or separate) display of a previous image serves to facilitate the navigation of the instrument in the vascular tree of the patient 2 by the physician. For example, a previous angiographic image offers a sort of vascular map (road map), or a previous image of the same medical intervention shows, for example, the position of a stenosis dilatated by a bulb catheter or the position of a previously placed first stent. In the latter cases the previous image assists the physician in repositioning the instrument to a previously adopted location.

For the usability of the previous image it is important that the position of the organs and vessels represented therein corresponds as accurately as possible to the situation in the current image. For given applications, and in the case of superposed reproduction of current and previous image, a precision in the range of a millimeter or even in the submillimeter range should be pursued.

The above precision is achieved in accordance with the invention in that the natural motion of the body volume itself, caused by heartbeat and/or respiration, is taken into account for associating a previous image from the memory 4 with the current image 8.

In order to enable the heartbeat to be taken into account, the ECG over the duration of the at least one heartbeat, during which the previous image was generated, as well as the instant of acquisition relative to the ECG are also stored in the memory 4 together with the previous images. Mapping the entire ECG cycle on the interval [0, 2π] enables the acquisition instant to be expressed as a value from this interval which reflects the relative heartbeat position of a previous image and subsequently serves as a first index of the previous image.

In order to enable the respiration to be taken into account, moreover, a second index is provided for the previous images; this second index reflects their relative position in the respiratory cycle. The second index is also typically normalized to the interval [0, 2π]. The second index can be derived, for example, from the measuring signals of a respiration sensor. Alternatively, the second index may also be acquired by way of a similarity comparison of the previous images with a reference image R which belongs to an extreme instant of the respiratory cycle (for example, "deep inhalation"). The second index of a given previous image then indicates its similarity distance relative to the reference image R and thus reflects the relative position in the respiratory cycle.

Said reference image R itself may have been selected from the previous images. In order to find an image from an extreme phase of respiration from among such previous images, for each previous image its similarity measures relative to a series of sequential images (over at least two respiratory cycles) can be calculated experimentally. If these similarity measures change, for example, periodically with approximately double the respiratory frequency, the experimentally considered previous image will be an image from a central phase of the respiratory cycle; however, if the similarity measures change periodically with approximately the single respiratory frequency, the previous image considered belongs to an extreme phase of the respiration so that it is suitable for use as a reference image R.

Various methods for associating a previous image with a current image will be described in detail hereinafter.

FIG. 2 shows a first method of association in accordance with the invention on the basis of a diagrammatic representation. The upper row shows the sequence of fluoroscopic live images of the body volume, in which a catheter 12 is propagated, on the monitor 6 of FIG. 1. One of these live images constitutes the "current image 8" on which the following explanation is based.

A respective previous image 10a, 10b, . . . is superposed on the live images on the monitor 7 of FIG. 1; these previous images are fetched from the memory 4 and updated at intervals. The previous images may be, for example, angiographic images showing the vascular tree in the body volume. The selection and association of a previous image 10a with the current image 8 takes place in three steps according to the first method of association:

First those images which have approximately the same similarity gap in respect of the respiratory cycle as the current image 8, relative to a predetermined reference image R, are selected from the memory 4. To this end, the current image 8 is compared with the reference image R, that is, a similarity measure r between the two images is calculated. Analogously, the similarity measures can be calculated between the reference image R and all previous images present in the memory 4. The latter has to be performed only once for a given quantity of previous images, because the measures do not change. As has already been explained, said measures may be normalized and be added as a (respiration) index to the previous images. Therefore, the amount of calculation work required during operation is comparatively small.

Using the similarity measures, or the indices, a sub-quantity U of the previous images can be determined whose members have approximately the same degree of similarity with respect to the reference image R as the current image 8. This means that the similarity measures of these images lie, for example, within a window r±Δ. If the memory 4 does not contain any image that satisfies this condition, the method of association is interrupted at this point.

However, if the sub-quantity U contains at least one element, a second selection in respect of the respiratory cycle is carried out in a second step. The previous images in the sub-quantity U are then individually compared with the current image 8, that is, the associated similarity measures r' are calculated and a sub-quantity V≦U is determined whose images exceed a limit value in respect of the similarity to the current image 8. The calculation-intensive individual comparison with the image 8 is minimized by the preselection of the quantity U.

Finally, in order to take into account the heart beat, in a third step that previous image 10a whose relative instant in the ECG is closest to the relative ECG instant of the current image 8 is selected from the sub-quantity V. For comparison between the electrocardiograms of the current image 8 and a previous image, a transformation is determined, for example, by means of a dynamic programming algorithm; this transformation maps the electrocardiograms on one another in an optimum fashion, thus enabling an exact prediction of the phase differences between the striking features (R, S, T lobes) of the electrocardiograms.

The described method of association can be modified in conformity with a first version in such a manner that first a sub-quantity of previous images is determined by ECG comparison. That one of the elements thereof which best matches the current image can then be determined by means of a direct comparison of the similarity to the current image.

A second version of the method of association utilizes the described indices of the previous images for the cardiac cycle and the respiratory cycle. Via these indices a point in a two-dimensional parameter plane can be associated with each previous image. A (usually elliptical) proximity can then be defined around the current image which is also represented in the parameter plane; previous images situated in this proximity (if any) then are potential candidates for the association. Among these candidates the best association can be found by direct comparison of similarity to the current image. A method of this kind offers the advantage that it enables the cardiac cycle and the respiratory cycle to be taken into account in combined form in the two-dimensional parameter plane.

In a post-processing step (not shown) subsequent to the association, an estimate of motion and a correction between the selected previous image 10a and the current image 8 can be carried out so as to compensate for changes due to a (whole body) motion of the patient.

For the above methods, for example, the histogram energy of the image differences is a suitable measure of similarity between two images. The images to be compared are then subtracted from one another one pixel after the other and the histogram of this difference image is calculated. The histogram indicates how many pixels n(G) of the difference image have each time a given grey scale value G. The similarity measure r is then calculated as the histogram energy which is by definition the square sum off all number of pixels:

$$r = \sum_G n(G)^2$$

This definition means that histograms with a concentration of the grey scale values have a high histogram energy, whereas histograms with an as uniform as possible distribution of the grey scale values over all pixels have a small histogram energy. The similarity measure r according to this definition, therefore, has a small numerical value when the compared images have a high degree of similarity, and vice versa A person skilled in the art can define alternative similarity measures on the basis of a local correlation or "mutual information".

The previous image 10a determined can be displayed on a monitor either separately or superposed on the current image 8. Because the association between the respective current image with a stored previous image usually cannot be continuously updated in real time but only (at least) once in every respiratory cycle, the user is additionally offered an indicator 11 which symbolizes the up-to-dateness of the instantaneously associated image. The indicator, for example, may change its color or, as is shown in FIG. 2, it may be a time bar 11 which becomes shorter as the association lasts longer. Fading of the superposed image 10a as a function of age of the association can also be perceived very well by intuition.

The invention claimed is:

1. An image processing unit which comprises:
   an input for the signal of a current image of a body volume, the body volume being subject to a motion comprising several phases of motion;
   at least one input for a signal which represents the phase of motion of the body volume which belongs to the current image;
   a memory in which previous images of the body volume are stored together with the associated phases of motion; and
   a controller for:
      calculation of a similarity measure between the current image and a representative image, the similarity measure being associated with the phase of motion;
      calculation of the similarity measure between the representative image and the previous images or a sub-quantity thereof; and
      selection of those previous images whose similarity measure relative to the representative image lies in a predetermined range around the similarity measure of the current image relative to the representative image,
   the image processing unit being arranged to associate with the current image that previous image from among the previous images whose phase of motion is closest to the phase of motion of the current image.

2. An image processing unit as claimed in claim 1, which is arranged to determine a distance between the phases of motion of the current image and an associated previous image and/or the time elapsed since the last association and to reproduce said distance for a user.

3. An image processing unit as claimed in claim 1, wherein the body volume is a biological body volume and the motion of the body volume is caused by heartbeat and/or respiration, and that the phase of motion is detected by means of an electrocardiogram and/or by the signal from a respiration sensor.

4. An image processing unit as claimed in claim 1, wherein the controller utilizes an extreme of a motion cycle of the body for the representative image.

5. An image processing unit as claimed in claim 1, which is arranged to carry out the following steps:
   selection of those previous images whose similarity to the current image exceeds a predetermined threshold value.

6. An image processing unit as claimed in claim 1, wherein together with each previous image there are stored the associated electrocardiogram and the relative instant of the image acquisition, and that the image processing unit is arranged to carry out the following steps:

determination of a transformation which maps the electrocardiograms of the current image and a previous image one onto the other; and determination of the relative position of the phase of motion of the current image and the previous image, as expressed in the electrocardiogram, by means of the transformation.

7. An image processing unit as claimed in claim 1, which is arranged to carry out a motion correction for a motion of the entire body volume between the current image and the associated previous image.

8. An image processing unit as claimed in claim 1, wherein said image processing unit is coupled to a reproduction unit and is arranged to reproduce the current image and the associated previous image in superposed form on the reproduction unit.

9. A method of associating a current image of a body volume which is subject to a motion comprising different phases of motion with one of several previous images of the body volume, in which method comprises the steps of:

determining the phase of motion together with obtaining a set of relevant images;

calculating a similarity measure between the current image and a representative image, the similarity measure being associated with the phase of motion;

calculating the similarity measure between the representative image and the previous images or a sub-quantity thereof; and selecting those previous images whose similarity measure relative to the representative image lies in a predetermined range around the similarity measure of the current image relative to the representative image, wherein the current image is associated with that one of the previous images which has a phase of motion closest to the phase of motion of the current image.

10. A method as claimed in claim 9, comprising determining at least one of a distance between the phases of motion of the current image and the associated previous image, and a time elapsed since the last association is determined and reproduced for the user.

11. An imaging device comprising:

a controller for obtaining a current image of a body volume and a phase of motion of the body volume which belongs to the current image, the body volume being subject to a motion comprising cardiac and respiratory motion; and a memory in which previous images of the body volume are stored together with associated phases of motion, wherein the controller calculates first and second similarity measurements between the current image and the previous images, the first similarity measurement being associated with a phase of one of the cardiac or respiratory motions, the second similarity measurement being associated with a phase of the other of the cardiac or respiratory motions, wherein the controller selects a first sub-quantity of the previous images based on the first similarity measurement, and wherein the controller selects an image from the first sub-quantity based on the second similarity measurement.

12. The device of claim 11, wherein the controller determines at least one of a distance between the phases of motion of the current image and the associated previous image, and an elapsed time since the last association.

13. The device of claim 11, wherein at least one of the first and second similarity measurements are performed on both the current and previous images using a representative image.

14. The device of claim 11, wherein the first and second similarity measurements comprise pixel subtraction between images to be compared.

15. The device of claim 11, wherein the controller performs motion correction for a motion of the entire body volume between the current image and the associated previous image.

16. The device of claim 11, further comprising a monitor that displays the current images superimposed with the selected image from the first sub-quantity of the previous images.

17. The device of claim 11, wherein at least a portion of the previous images are obtained from an ultrasound process, magnetic resonance imaging and scintigraphy.

18. The device of claim 17, wherein the current image is obtained using x-ray imaging.

19. The device of claim 11, wherein the representative image is from an extreme of a cardiac or respiratory motion cycle.

20. The method of claim 9, further comprising associating a point in a two dimensional parameter plane with each of the previous images, wherein the association is based on mapping of both a cardiac cycle and a respiratory cycle of the body volume.

* * * * *